US00PP20866P2

(12) United States Plant Patent
van Kleinwee

(10) Patent No.: US PP20,866 P2
(45) Date of Patent: Mar. 23, 2010

(54) ***ARGYRANTHEMUM FRUTESCENS* PLANT NAMED 'J0208-1'**

(50) Latin Name: *Argyranthemum frutescens*
Varietal Denomination: J0208-1

(75) Inventor: Theodorus Cornelis Maria van Kleinwee, Hoorn (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/321,672

(22) Filed: Jan. 23, 2009

(51) Int. Cl.
*A01H 5/00* (2006.01)

(52) U.S. Cl. ..... Plt./406

(58) Field of Classification Search ..... Plt./263, Plt./406

See application file for complete search history.

*Primary Examiner*—Susan B McCormick Ewoldt
(74) *Attorney, Agent, or Firm*—S. Matthew Edwards

(57) ABSTRACT

A new *Argyranthemum* plant named 'J0208-1' particularly distinguished by its vigorous round plant habit with dark green foliage, and its early, rich and long flowering with white flowers with a dark red center.

1 Drawing Sheet

Latin name of the genus and species of the plant claimed: *Argyranthemum frutescens.*

Varietal denomination: 'J0208-1'.

BACKGROUND OF THE NEW PLANT

The present invention relates to a new and distinct cultivar of *Argyranthemum* plant, botanically known as *Argyranthemum frutescens* and hereinafter referred to by the cultivar name 'J0208-1.' The new cultivar is a product of a planned breeding program conducted in Enkhuizen, Netherlands.

The new *Argyranthemum* originated from an open pollination conducted in a controlled environment in Enkhuizen, Netherlands in 2004 of a proprietary selection of *Argyranthemum frutescens* identified as code number 'B0050-1,' not patented, as the female, or seed, parent with pollen of unknown *Argyranthemum fruiescens* plants as the male, or pollen, parent.

The cultivar 'J0208-1' was discovered and selected as a single plant within the progeny of the stated open pollination in Enkhuizen, Netherlands, in August 2005. The new *Argyranthemum* has been repeatedly asexually reproduced in Enkhuizen, Netherlands since August 2005. The distinctive characteristics of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'J0208-1' and distinguish to new *Argyranthemum* as a new and distinct cultivar:

1. Round plant habit.
2. Early flowering habit.
3. Freely flowering habit with numerous inflorescences per plant.
4. Dark green foliage.

5. Strong vigor.
6. White flowers with a dark red centre.

Plants of the new *Argyranthemum* differ from plants of the female parent in the following characteristics:

'J0208-1' has flowers with a dark red center while the female parent has flowers with a greenish-yellowish center.

'J0208-1' has a round plant habit while the female parent has a more upright plant type.

'J0208-1' has rather long peduncles while the female parent has very short peduncles.

Differences between plants of the new *Argyranthemum* and plants of the male parent are unknown, as the male parent is unknown.

TABLE 1

DIFFERENCES BETWEEN THE NEW CULTIVAR 'J0208-1' AND THE SIMILAR CULTIVAR 'ARGYDOWITIS'

| | 'J0208-1' | 'Argydowitis' (U.S. Plant Pat. No. 15,904) |
|---|---|---|
| Plant vigor | Medium | Medium to strong |
| Peduncle length | Medium to long | long |
| Disc florets color | Pink | White |

DESCRIPTION OF THE PHOTOGRAPHS

The accompanying color photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Argyranthemum.*

DESCRIPTION OF THE NEW CULTIVAR

The aforementioned photographs, following detailed observations and averaged measurements describe plants of this new Marguerite Daisy plant. The data were collected from plants from asexual reproductions carried out in Enkhuizen, Netherlands. The plant history was taken on plants of 15 weeks old, grown in the open field in Enkhuizen, Netherlands, with day temperatures ranging from 16 to 35° C., and night temperatures ranging from 10 to 20° C.

Color references are primarily to the RHS Colour Chart of The Royal Horticultural Society, 2001 Edition, except where general terms of ordinary dictionary significance are used.

The plant:

*Classification — Botanical.*—*Argyranthemum frutescens.*

Parentage:

*Female parent.*—Proprietary selection of *Argyranthemum frutescens* identified as number 'B0050-11' (not patented).

*Male parent.*—Unidentified plants of *Argyranthemum frutescens.*

Propagation:

*Type of cuttings.*—Terminal cuttings.

*Time to intiate roots.*—7–10 days at air temperature of 21° C.

*Time to develop roots.*—7–14 days at air temperature of 18° C.

*Root description.*—Fibrous, fine, white in color.

*Rooting description.*—Freely branching, dense.

Plant description:

*Growth habit.*—Round shape.

*Plant height.*—20 cm.

*Vigor.*—Very vigorous.

*Spreading area.*—40 cm.

*Branching character.*—Freely branching, plants do not require pinching.

*Crop time.*—About 9 weeks are required to produce a finished flowering plant in a 10.5 cm container from a well developed cutting.

Lateral branch description:

*Length.*—20 cm.

*Diameter.*—3–5 mm.

*Shape.*—Round, slightly grooved.

*Anthocyanin pigmentation.*—Present, color N200A.

*Texture.*—Smooth, glabrous.

*Length of internode.*—1–1.5 cm.

*Pubescence.*—Absent.

*Color.*—147D.

The foliage:

*Arrangement.*—Alternate, simple.

*Shape.*—Bipinnatisect.

*Apex.*—Broadly acute.

*Base.*—Attenuate, clasping.

*Margin.*—Deeply dissected, laciniate.

*Texture.*—Smooth, glabrous.

*Length.*—3–5 cm.

*Width.*—2–3 cm.

*Color.*—Upper side: 138B. Lower side: 138B.

*Pubescence.*—Absent.

*Petiole.*—Length: 1.5–2 cm. Diameter: 2 mm. Texture: Smooth, glabrous. Color: 138B.

*Venation.*—Shape: Pinnate. Color: 143C.

The inflorescence:

*Appearance.*—Daisy-type inflorescences with ligulate ray florets and well developed disc florets. Disc and ray florets develop acropetally on a capitulum. Inflorescences held upright and outwardly on terminal and axillary peduncles. Inflorescences positioned perpendicular to the peduncles. Inflorescences persistent.

*Flowering period.*—Under natural conditions, plants flower continuously from spring to early fall.

*Inflorescence longevity.*—10 days.

*Quantity of inflorescences.*—Freely flowering, about 150 open inflorescences and 300 inflorescence buds per plant.

The flower bud:

*Peduncle.*—Length: 5–6 cm. Diameter: 1.5 mm. Strength: Strong. Aspect: Upright to slightly outward. Texture: Smooth, glabrous. Color: 138B.

*Inflorescence bud* (*just before opening*).—Height: 6 mm. Diameter: 7 mm, just before moment of opening of flower. Shape: Ovoid. Color: 199C.

The inflorescence:

*Size.*—Diameter: 3 cm. Depth: 10 mm.

*Disc diameter.*—13 mm.

*Receptacle.*—Height: 6 mm. Diameter: 5 mm.

*Involucre.*—Number of bracts: Approximately 20 bracts, not organized in whorls. Shape: Elliptic. Apex: Broad. Base: Truncate. Texture: Smooth, glabrous. Margin: Entire. Length: 2–4 mm. Width: 1 mm. Color upper and lower side: 138B; towards peduncle 152A.

*Fragrance.*—Absent.

Ray florets:

*Quantity per inflorescence.*—Approximately 13, in one whorl.

*Shape.*—Ligulate.

*Apex.*—Emarginate.

*Base.*—Attenuate.

*Margin.*—Entire.

*Color upper surface.*—Whiter than N155D.

*Color lower surface.*—Whiter than N155D.

*Length.*—1 cm.

*Width.*—0.4 cm.

*Texture.*—Smooth, glabrous; longitudinally ridged.

Disc florets:

*Arrangement.*—Massed at the center of the inflorescence.

*Shape.*—Tubular, elongated, five-pointed; base fused.

*Color.*—Immature: 53A. Mature: 49D.

*Diameter.*—Apex: 2 mm. Base: <1 mm.

*Length.*—0.6 cm.

*Quantity per inflorescence.*—Approximately 150.

*Androecium.*—Presence: Absent on ray florets; present on disk florets. Stamen quantity per floret: 5. Anther length: 1 mm. Anther shape: Oval. Anther color: 17A. Pollen color: 17A. Amount or pollen: Abundant.

*Gynoecium.*—Presence: Present on ray and disc florets. Number of pistils per floret: 1. Pistil length: Approximately 3 mm. Style color: Lighter than 155D. Style length: Approximately 1 mm. Stigma color: 14A. Stigma shape: Bilobed. Ovary color: 157D.

Seed and fruit development: Seed and fruit development has not been observed.

Disease resistance: No disease/pest resistance has been observed to date.

Temperature/weather tolerance: Plants of the new *Argyanthemum* have been observed to be tolerant to rain, wind and to temperatures from 0° C. to 36° C.

What is claimed is:

1. A new and distinct variety of *Argyranthemum* plant, named 'J0208-1,' as substantially illustrated and described herein.

* * * * *

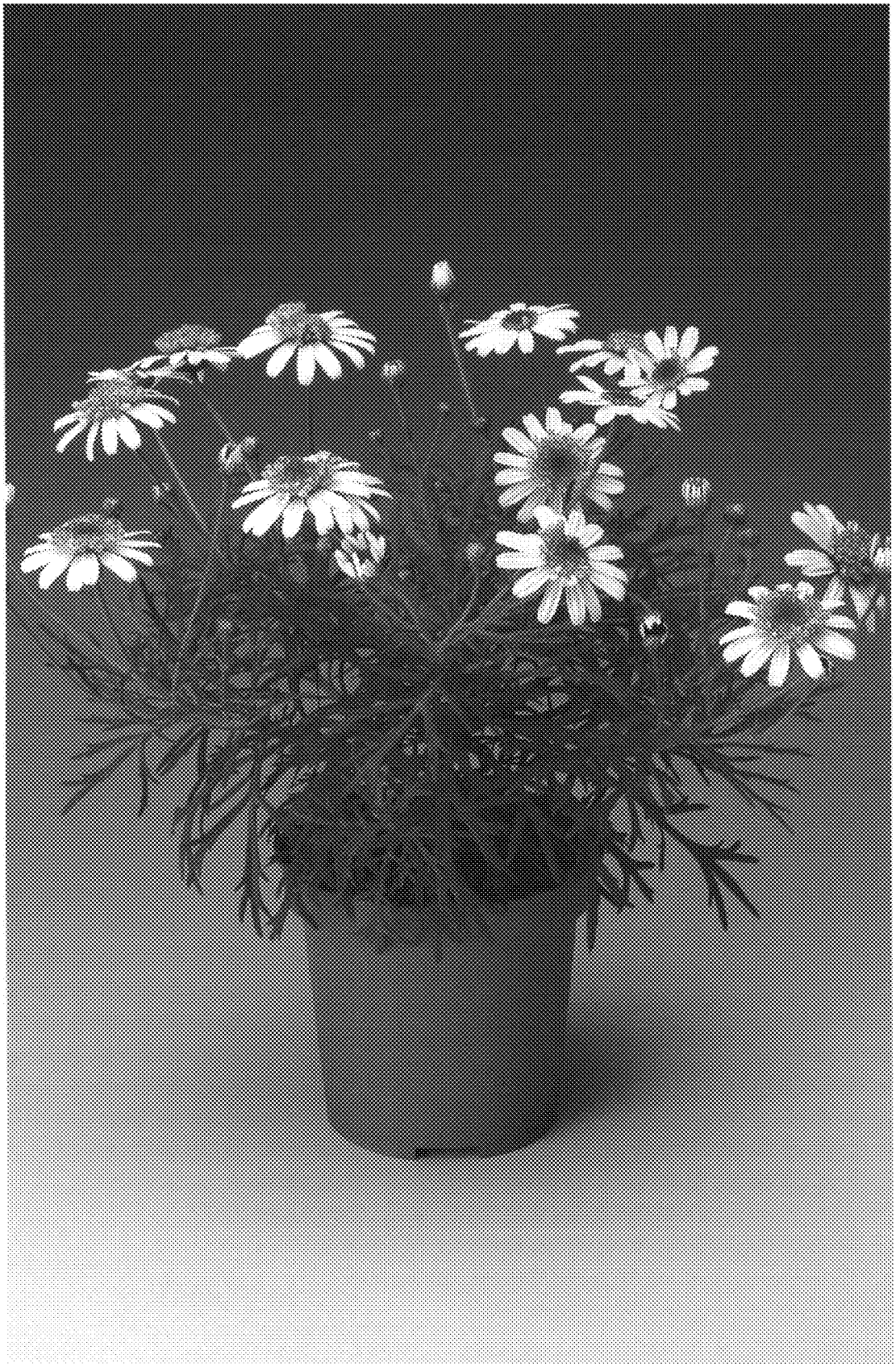

UNITED STATES PATENT AND TRADEMARK OFFICE

CERTIFICATE OF CORRECTION

PATENT NO. : PP 20,866 P2
APPLICATION NO. : 12/321672
DATED : March 23, 2010
INVENTOR(S) : Theodorus Cornelis Maria van Kleinwee It is certified that error appears in the above-identified patent and that said Letters Patent is hereby corrected as shown below:

At column 3, line 14, delete "'B0050-11'" and insert therefor --'B0050-1'--

Signed and Sealed this

Eleventh Day of May, 2010

David J. Kappos

David J. Kappos
*Director of the United States Patent and Trademark Office*